United States Patent [19]

Yaverbaum et al.

[11] Patent Number: 4,576,912

[45] Date of Patent: Mar. 18, 1986

[54] FLUOROIMMUNOASSAYING

[75] Inventors: Sidney Yaverbaum, East Windsor, N.J.; Jacob Kusnetz, New City, N.Y.

[73] Assignee: Technicon Instruments Corporation, Tarrytown, N.Y.

[21] Appl. No.: 470,516

[22] Filed: Feb. 28, 1983

Related U.S. Application Data

[63] Continuation-in-part of Ser. No. 965,118, Nov. 30, 1978, abandoned.

[51] Int. Cl.$^4$ .................. G01N 53/00; G01N 33/553; G01N 33/544; G01N 33/542
[52] U.S. Cl. ........................................ 435/7; 436/526; 436/528; 436/529; 436/530; 436/531; 436/537; 436/800; 436/807; 436/810
[58] Field of Search .................. 424/1, 1.5, 8, 12; 436/536, 546, 528–531, 537, 800, 807, 526, 810; 435/7

[56] References Cited

U.S. PATENT DOCUMENTS

| | | | |
|---|---|---|---|
| 4,000,252 | 12/1976 | Kosak | 424/12 X |
| 4,039,652 | 8/1977 | Adams | 424/12 X |
| 4,108,972 | 8/1978 | Dreyer | 424/12 |
| 4,133,873 | 1/1979 | Nollor | 23/230 B |
| 4,231,999 | 11/1980 | Carlsson et al. | 436/804 X |
| 4,272,506 | 6/1981 | Schwarzberg | 436/800 X |
| 4,279,992 | 7/1981 | Boguslaski et al. | 436/800 X |
| 4,320,109 | 3/1982 | Wolf et al. | 436/540 |

FOREIGN PATENT DOCUMENTS 2537275  2/1977  Fed. Rep. of Germany .......... 424/8

*Primary Examiner*—Christine M. Nucker
*Attorney, Agent, or Firm*—Morgan, Finnegan, Pine, Foley & Lee

[57] ABSTRACT

A method of composition is featured for performing a fluoroimmunoassay of a biological fluid sample for an immunological reactant. A conjugate of a carrier labelled with fluorophores and coupled to an immunological reactant is mixed with the sample and a known quantity of binding agent. After equilibrium is accomplished, the bound and unbound portions are separated. The carrier in a selected portion is chemically treated to liberate the fluorophores. The fluorescent level is then measured and compared with a standard.

14 Claims, 6 Drawing Figures

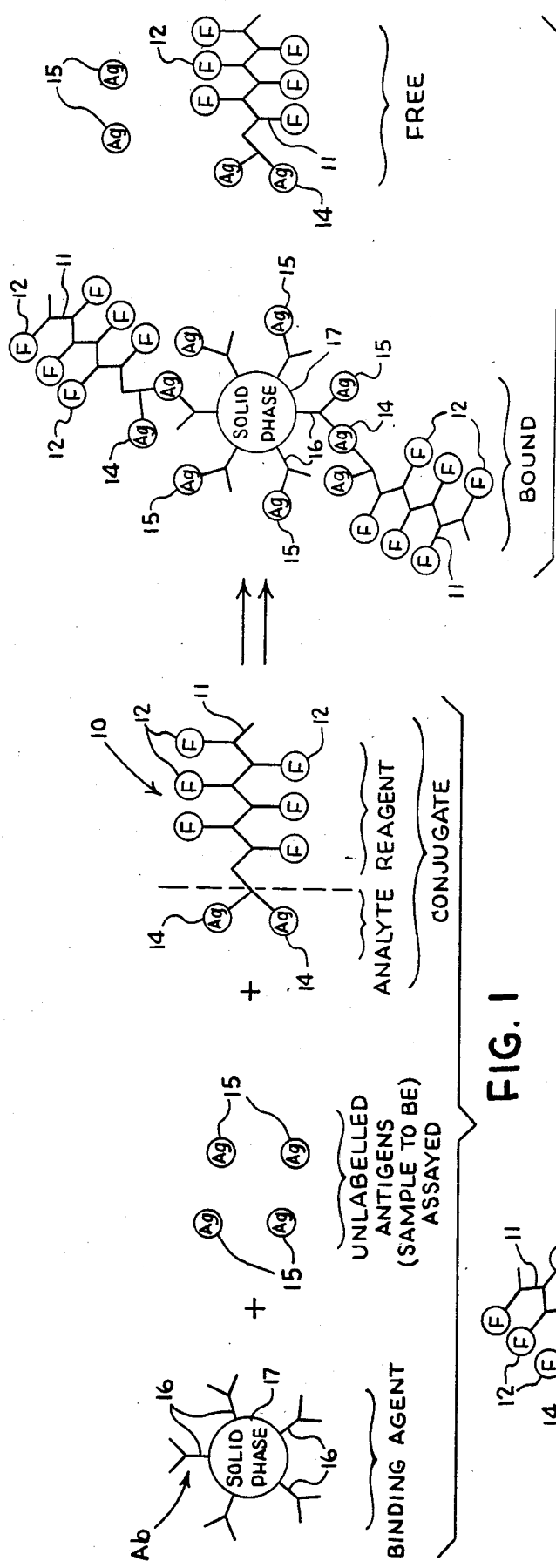
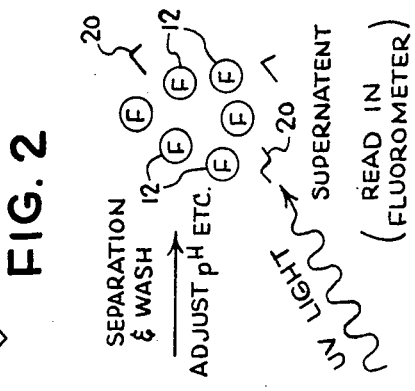
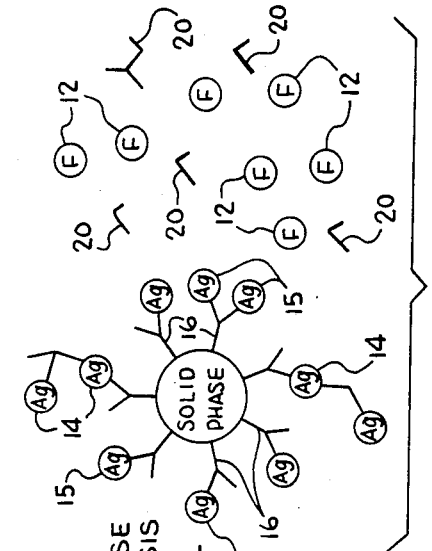
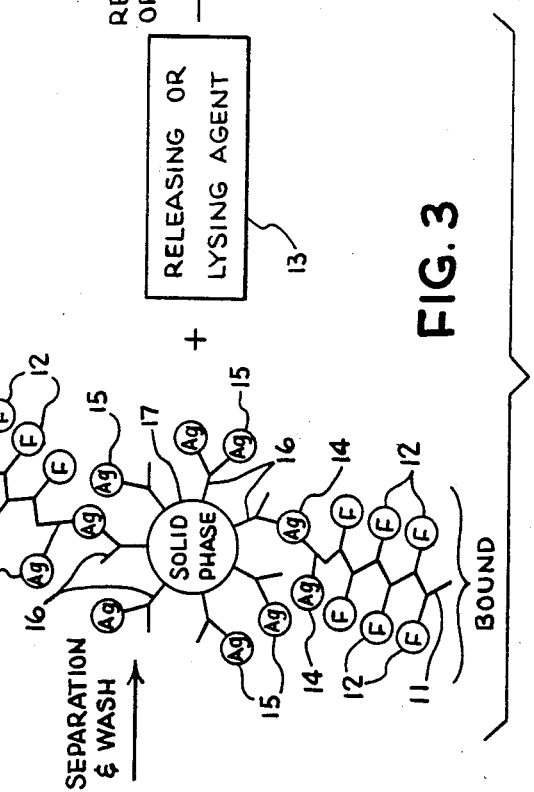

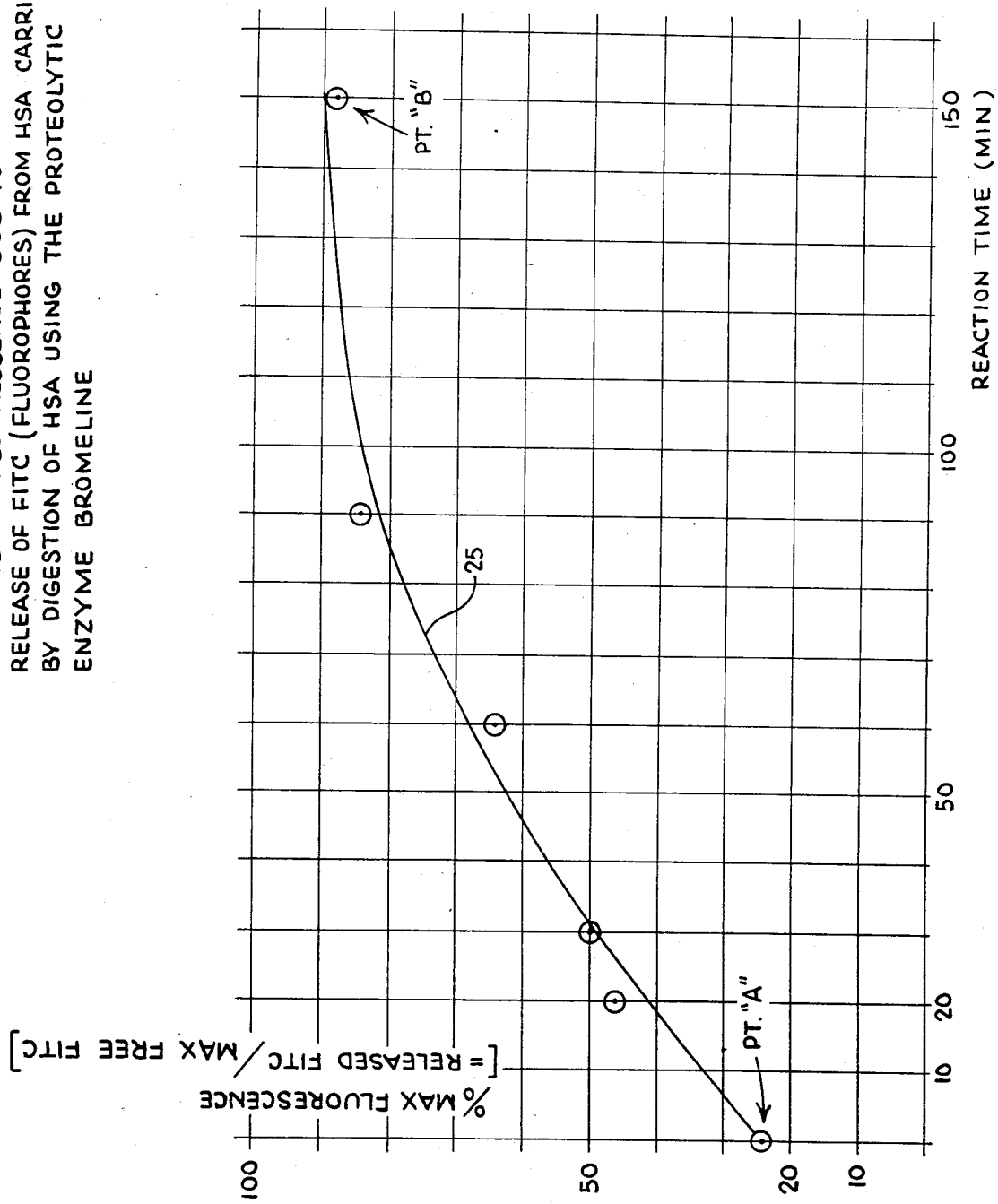

FLUOROIMMUNOASSAYING

CROSS-REFERENCE TO RELATED APPLICATION

This is a continuation-in-part of Application Ser. No. 965,118, filed Nov. 30, 1978, now abandoned.

FIELD OF THE INVENTION

The invention relates to a method and compositon for performing a fluoroimmunoassay of a biological fluid sample and, more particularly, for performing a more sensitive fluoroimmunoassay using a conjugate formed by heavily fluorescently tagging a carrier, to the extent that self-quenching between the bound fluorophores may take place, which is subsequently chemically treated to liberate the fluorophores for measurement.

BACKGROUND OF THE INVENTION

It is known that a greater sensitivity can be achieved in a fluoroimmunoassay, if the competitive reactant is heavily labelled. However, as the number of fluorophores bound to such reactant is increased, the spacing between adjacent fluorophores decreases until a critical distance of 60 Å to 100 Å is reached. At this critical distance, or less, the fluorophores are self-quenching, i.e., the fluorescent level becomes less than an equivalent number of fluorophore molecules distanced greater than 100 Å. Quenching also occurs in certain assays, e.g., for thyroid hormones, because of the iodine present in such materials. In the past, fluorometric assays for these reactants have been extremely difficult.

The invention heavily labels a competing ractant with fluorophores, which may be subjected to self-quenching, and then the fluorophores are separated from the reagent after competitive binding has occurred. Following separation, the fluorophores are spaced beyond the critical distance, whereby self-quenching ceases and the available fluorescent level is restored. Accordingly, a more sensitive fluoroimmunoassay can achieved.

SUMMARY OF THE INVENTION

This invention pertains to a method and reagent for performing a fluoroimmunoassay using a heavily labelled reagent which competes with the immunological reactant in the sample for a known quantity of a complementing binding agent. The reagent comprises a conjugate formed by tagging a plurality of fluorophores to a carrier capable of being chemically treated, so as to release the fluorophores. The reagent is coupled to a competitive reactant to form a conjugate. The sample and the conjugate are mixed with a binding agent. After the competitive-binding reaction, the bound immunological reactants and unbound immunological reactants are separated. The carrier, in either or both separated portions, is then chemically treated, or lysed, to liberate the otherwise quenched, closely-packed fluorophores to greatly enhance the fluorescent level. The fluorescent level of the liberated fluorophores is then compared to a standard level of fluorescence to determine the amount of immunological reactant in the sample.

In another embodiment of the inventive method, the fluorophores are directly labelled to a competing reactant without the need for a carrier. In this case, the competing reactant must be chemically treatable to liberate the fluorophores.

Preferably, carriers are selected to have many fluorophorebinding sites whereby a large number of fluorophores can be attached thereto. As the probelm of self-quenching is avoided by this invention, a large number of binding sites are preferred. For example, such carariers may be very long chain molecules such as proteins, polymers, or polysaccharides.

The reactant in the biological fluid sample may be either an antigen or an antibody. The competing immunological reactant conjugated with the carrier will be a corresponding antigen or antibody or, in some cases, a hapten.

It is an object of this invention to provide an improved method and reagent for performing a fluoroimmunoassay.

It is another object of the invention to provide a more sensitive fluoroimmunoassay.

These and other objects of the invention are achieved by: conjugating one reactant of said fluoroimmunoassay with a carrier tagged with a plurality of fluorophores to provide a quenched level of fluorescence; and liberating the fluorophores from said carrier following reaction with its complement.

BRIEF DESCRIPTION OF THE DRAWINGS

Additional objects and features will become more apparent from the following detailed description taken in conjuction with the accompanying drawings, in which:

FIG. 1 depicts the formation of a mixture comprising the fluid sample, the competing conjugate, and a binding agent;

FIG. 2 shows the equilibrated products of the mixture of FIG. 1;

FIG. 3 illustrates a separated portion of the equilibrated products of FIG. 2;

FIG. 4 depicts the products of FIG. 3; following liberation of the fluorophores previously bound to the carrier.

FIG. 5 shows the liberated fluorophores after separation and wash from the products of FIG. 4; and FIG. 6 illustrates a graph depicting the increase in fluorescent level prior to and following liberation of the fluorophores from the carrier.

DETAILED DESCRIPTION

Generally speaking, the inventive method for assaying a fluid sample for a reactant comprises the steps of: (a) using a reagent comprising a tagged carrier capable of being coupled to a competing reactant to form a conjugate. The tagged carrier has a plurality of fluorophores. When the carrier is treated chemically, the fluorophores release from the carrier. After a conjugate is formed by coupling a competing reactant to the tagged carrier reagent; (b) a mixture is then formed of the sample, a known amount of the conjugate and a binding agent; (c) after equilibration, the mixture is separated into a first bound and a second unbound portion, i.e., unbound conjugate reactant and unbound sample reactant are removed from the bound conjugate reactant and bound sample reactant; (d) to either the first bound portion or the second unbound portion of the mixture, an enzyme, lysing agent or other chemical reagent is added to liberate the tagged fluorophores; (e) the fluorescent level of the liberated fluorophores is measured and compared with a standard fluorescent level.

Now referring to FIG. 1, the conjugate 10 of method step (a) is shown. The conjugate 10 is formed by fluorescently tagging (labeling) a carrier molecule 11 with as many fluorophores 12 as possible. The carrier molecule 11 is a long chain molecule having many fluorophore binding sites. Such a molecule can be a protein, cellulose, a cellulose derivative, a polysaccharide a polymer, etc. The carrier 10 must be capable of either being lysed by an enzyme or other lysing agent 13 (FIG. 3), or treated chemically to free the fluorophores. The tagged carrier is the inventive reagent which will enhance the fluorescent level of the immunoreaction, whereby the sensitivity of the assay will be greatly improved.

To this reagent, a reactant such as an antigen (Ag) a hapten, or an antibody (Ab) is coupled to form the conjugate 10. In the illustration of FIG. 1, antigens (Ag) 14 have been coupled to the carrier 11. The antigens (Ag) 14 compete with antigens (Ag) 15 in the fluid sample.

Antibodies 16 will bind with either antigens 14 or antigens 15. As described, antibodies 16 are bound to a solid phase 17, to form a binding agent, as is well known in the art. The solid phase 17 can be magnetic particulate cellulose, glass, latexes, plastics, agaroses, sepharoses, and sephadexes, etc. The solid phase particulate may be shaped as spheres, rods, tubes or some other generally uniformly-shaped particles, etc.

As shown in FIG. 1, a mixture is made of the sample containing an unknown amount of antigens 15, a known amount of the conjugate 10 and a known amount of binding agent. The binding agent will equilibrate with the antigens 14 and 15, respectively, as aforementioned, to form the reaction products shown in FIG. 2. The mixture now contains bound and unbound, or free, fractions, i.e., bound molecules comprising antigenantibody linkages, and unbound molecules containing free antigens 14 and free antigens 15.

FIG. 3 illustrates the bound product portion of the product mixture of FIG. 2 after separation and washing. The bound product portion is treated with an appropriate enzyme or lysing agent 13, that will digest or lyse the long chain carrier molecule 11.

In one embodiment of this invention, the carrier 11 may be treated chemically to release the fluorophores 12 which are bound to it, by breaking-up the carrier molecule. By way of example, a protein molecule carrier may be lysed by enzymes such as: pepsin, bromalin, trypsin, chymotrypsin, papain, pronase, etc. Where a cellulose molecule is used as the carrier, a cellulase enzyme such as emulsin may be used. Where the carrier is a polysaccharide such as dextran, a dextranase enzyme can be employed.

The results of the lysing of carrier 11 by the enzyme 13 are shown in FIG. 4. The carrier 11 will be lysed into many fragments 20, to liberate the fluorophores 12. The liberating of the fluorophores 12 allows them to become spaced apart in solution, thus freeing their fluorescent characteristics and avoiding any self-quenching effects. The fluorescent level will be proportional to the number of antigen-antibody reactions that have taken place. Therefore, the measured fluorescent level of the liberated fluorophores 12 can be compared to a standard level of fluorescence in order to determine the amount of antigens 15 in the sample.

As aforementioned, the unbound or free portion of FIG. 2, may also be treated with an enzyme 13 to obtain a fluorescent level proportional to the number of competing antigen-antibody reactions. The amount of antigens 15 in the sample may likewise be obtained from this data, because a known amount of reagent and binding agent are used in the reaction. The fluorescent level of the free portion, therefore, can similarly be compared to a standard fluorescent level. Where the free or unbound portion is treated, the additional separation and washing step of FIGS. 4 and 5 will not be necessary.

As is known in the art, the bound reaction products of FIG. 4 are separated and washed, and appropriate adjustment in pH or other conditions are made in the solution, as depicted in FIG. 5. The fluorophores 12 are then subjected to ultraviolet light, and the fluorescence is measured in a fluorometer.

The fluorophores 12 which may be used in the invention are those generally available for these procedures, such as: fluorescein, dansyl, rhodamine, fluorescamine, pyrene, acridine and 2-methoxy-2,4-diphenyl-3(2H)-furanone (MDPF). It may be found that certain ones of these fluorophores will provide better binding to certain ones of the carriers 11, or will provide a higher level of fluorescence as will be obvious to those skilled in the art.

Referring to FIG. 6, a curve 25 illustrates the released fluorescence vs. time, of fluorescein tagged molecules of Human Serum Albumin (HSA), which have been digested by the proteolytic enzyme Bromelin. Point "A" depicts the initial level of fluorescence prior to the digestion of the HSA molecule; about 25% of the maximum expected level of fluorescence for a free amount of unbound fluorescein.

As the HSA molecule is digested by the Bromelin, an increasing amount of fluorophores are released, and the fluorescent level is increased. As the HSA molecule is completely digested by the bromelin, i.e., after a reaction time of approximately 150 minutes, almost all of the fluorophores will be released to give a fluorescent level approaching 90% of maximum, as shown by point "B".

FIG. 6, therefore, shows that a carrier molecule 11, such as fluorescein-labeled HSA, can function to enhance a flurorimmunoassay of an antigen or antibody, according to the outlined method.

Where the molecule can be lysed by more than one enzyme, several enzymes may be simultaneously used to break up the carrier molecule into finer segments. This will give rise to a greater fluorescence. For example, in a protein molecule carrier, trypsin will cleave the protein molecule at amino acid linkages arginine and lysine. If the enzyme chymotrypsin is also used to digest the protein, the additional amino acid linkages of phenylalanine, leucine, and tyrosine will also be cleaved. Thus, the protein molecule will be broken into smaller segments, and hence, the attached fluorophores will enjoy a greater release into the solution. Consequently, a greater fluorescent level should be obtained.

In another embodiment of the inventive method, it is contemplated to liberate the fluorophores from a protein or polymer molecule without the necessity of having to lyse or digest the carrier molecule. In an article to Martin J. Lee, Ph.D., et al entitled: "The Inhibition of Mitrochondrial Energized Processes by Fluorescein Mercuric Acetate"; Bioenergetics (1971) 2, pp. 13–31; it is taught that fluorescent molecules such as Fluorescein Mercuric Acetate can attach reversibly to sulfhydylo groups (SH) of proteins and other polymers. These fluorophores can be released by agents such as dithiothreitol.

The invention envisions using this technique to enhance the fluorescent level in a fluoroimmunoassay as previously described herein. The liberation of the fluorophores from the reactant carrier conjugate without the need for lysing suggests an alternate embodiment to the invention which may provide certain advantages such as quicker release time for the fluorophores. This procedure will be particularly useful where the carrier contains many sulfhydryl groupings, such that the carrier can be heavily labeled.

Also, where reactants themselves can be tagged fluorescently, it may be advantageous to bind and then liberate the fluorophores directly to and from the reactant without need for a carrier molecule. This alternate embodiment to the inventive method will be useful where the reactant is a long chain molecule that can be heavily tagged, or where the fluorescence is completely quenched as in the case of the thyroid hormone assay.

EXAMPLE I

Preparation of Thyroxine-Human Serum Albumin Conjugate ($T_4$-HSA)

Sodium thyroxine $NaT_4$ (36.72 mg) was dissolved in a mixture of absolute methanol (1 ml) and 0.1 N sodium hydroxide solution (0.25 ml). To the resulting solution was added $I^{125}$-$T_4$ (radio-labeled iodinated thyroxine, 0.25 ml; total 251,610 cpm) and 0.15 M phosphate buffered saline (5.2 ml) having a pH 7.5. The resulting solution was added to a solution of human serum albumin (125 mg) in water (6.25 ml). To this was added 1-ethyl-3-(3-dimethylaminopropyl)carbondiimide (13.12 mg) and the mixture was stirred overnight at room temperature.

The reaction mixture was dialysed against water (changes of 3l each) until completed (i.e. radioactive thyroxines could not be found outside the dialysis bag. The reaction mixture was then clarified by centrifugation. The ratio of $T_4$ per protein molecule was 7.3 as determined by counting conjugated $I^{125}$-$T_4$ and estimating protein concentration from its absorption at 280 nm. The protein concentration is 17 mg/ml.

EXAMPLE II

Preparation of Thyroxine-Fluorescein-Human Serum Albumin Conjugate

To a mixture of the conjugate of Example I (0.59 ml) and 4.4 ml of sodium carbonate buffer (0.1 M, pH 9.0) was added fluorescein isothiocyanate FITC (1.0 mg). The resulting stirred mixture was incubated overnight at 4° C. and then separated on a Sephadex G-25 column (2.5 cm×40 cm) equilibrated with 0.05 M phosphate buffer, pH 7.35. After separation of the conjugate from free FITC, the amount of fluorescein which became conjugated was 3.7 per molecule of HSA as estimated from its absorption at 495 nm. This amount of fluorescein is indicative of a fluorophore spacing distance of less than 100 Å.

EXAMPLE III

Binding of Thyroxine-Fluorescein-HSA Conjugate to Anti-Thyroxine Antibody on Magnetic Particles Anti-thyroxine magnetic particles (available from Technicon) (20 mg) and conjugate (0.04 ml) as prepared by Example II (total 130 μg of HSA) were mixed in 1 ml of 0.05% HSA/phosphate buffered saline, pH 7.4 and incubated for 60 min. at room temperature. The particles were then separated with a magnet and washed 4 times each with a 0.4 ml buffer. The amount of a conjugate which became bound is calculated by counting the bound radioactive thyroxine. Alternatively, the bound conjugate can be determined by measuring radioactivity in solution whereby the bound conjugate is eluted by incubating the particles in 0.1 N NaOH solution for 30 min. at room temperature.

The results showed binding of 26 μg of the conjugate.

EXAMPLE IV

Increase of Fluorescence of Conjugate Solution After Enzymatic Digestion With Bromelin 0.25 ml of conjugate solution as prepared in Example II was incubated with 1.75 ml of bromelin (1200 units) in 0.05 M phosphate buffer pH 7.0. The mixture was incubated at 36° C. and aliquots of 0.1 ml each were removed at various times and diluted 1:125 with buffer for fluorometric analysis. Measurements were done with Aminco-Bowman spectrofluorometer. Excitation was at 495 nm and emission was scanned between 450–650 nm. Actual readings were taken at 550 nm. The fluorescence increases as the enzymatic digestion proceeds as shown in the Table below.

| Incubation Time With Bromelin (min.) | Relative Fluorescence of $T_4$-$I^{125}$-$T_4$-FITC-HSA Solution |
| --- | --- |
| 0 | 1 |
| 20 | 1.9 |
| 30 | 2.1 |
| 60 | 2.7 |
| 90 | 3.5 |
| 150 | 3.7 |

EXAMPLE V

The procedure of Example 4 is repeated to demonstrate the increase of fluorescence of the bound conjugate of Example III by enzymatic digestion except that prior to analysis the lysed product is separated from particles by a magnet and the pH adjusted to 11.0 by the addition of equal volume of 0.1 M sodium carbonate.

The spectrofluorometric analysis showed similar results.

EXAMPLE VI

The procedure of Example V is repeated for the non-isotopic conjugate of Example II with similar results.

EXAMPLE VII

A biological specimen (50 μL, human serum) is combined with the conjugate as prepared by Example II (10 μg/50 μL and anti-thyroxine magnetic particles (1 mg/50 μL) and incubated at 37° C. for a period of 30 min.

The magnetic particles are separated by a magnet and washed once with 1 ml buffer and is then incubated for 60 min. at 36° C. with bromelin (2400 units) in 0.05 M phosphate buffer, pH 7. The particles are then separated by a magnet and the fluorescence of the resulting solution is measured as in Example V.

The fluorescence of the liberated fluorophores is compared with a standard to determine the amount of immunological reactant in the sample.

Having described the invention, what is desired to be protected by Letters Patent is presented in the following appended claims.

What is claimed is:

1. A method of enhancing the fluorescent level of a fluoroimmunoassay, comprising the steps of:
    (a) tagging a long-chain carrier selected from proteins, cellulose, cellulose derivatives, polymers or polysaacharides, said carrier having fluorophore binding sites and capable of treatment to release fluorophores bound thereto, with a plurality of fluorophores, said fluorophores selected from the group consisting of fluorescein, dansyl, rhodamine, fluorescamine, pyrene, acradine, 2-methoxy-2,4-diphenyl-3(2H)-furanone, and fluorescein mercuric acetate until a critical spacing distance of less than 100 Å is reached between said fluorophores to induce self-quenching therebetween;
    (b) conjugating one reactant of said fluoro-immunoassay with said fluorescently-quenched carrier;
    (c) reacting said conjugated reactant in a known amount with a competing immunoreactant sample and a known amount of a complementary-reactant-containing solid phase binding agent to form a mixture of bound and unbound reaction products, said solid phase binding agent selected from magnetic particulate cellulose, glass, latexes, plastics, agaroses, sepharoses and sephadexes;
    (d) separating said bound and unbound reaction products;
    (e) liberating the fluorophores from said carrier following said separation in either one of the bound or unbound reaction product by breaking up the carrier molecule by a lysing or chemical treatment; and
    (f) measuring the enhanced fluorescent level of said liberated fluorophores.

2. The method of claim 1, wherein the step (e) further comprises the step of lysing said carrier by at least one enzyme.

3. The method of claim 1, wherein said conjugated reactant is an antigen, an antibody or a hapten.

4. The method of claim 1 wherein said fluorescently-quenched carrier is fluorescein-human serum albumin and said phase binding agent is comprised of magnetic particles.

5. A method of fluoroimmunoassaying a fluid sample for an immunological reactant, comprising the steps of:
    (a) forming a mixture of a sample containing an immunological reactant to be assayed with a known amount of a fluorescently self-quenched, fluorophore tagged competing immunological reactant wherein the spacing distance between fluorophores is less than 100 Å, and a known amount of a complementary-reactant-containing solid phase binding agent that equilibrates with both said sample reactant and said competing reactant;
    (b) equilibrating said mixture to form a first portion comprising reactants bound to said binding agent, and a second portion comprising reactants which are not bound to said binding agent;
    (c) separating the mixture into said first and second portions, respectively;
    (d) liberating fluorophores from said tagged immunological reactant in either one of said first or second portions by a lysing or chemical treatment; and
    (e) measuring the fluorescent level of said liberated fluorophores.

6. The method of claim 5, wherein said immunological reactant is an antigen and said binding agent is an antibody which specifically binds to said antigen.

7. The method of claim 5, wherein said immunological reactant is an antibody and said binding agent is an antigen which specifically binds to said antibody.

8. The method of claim 5, wherein said solid phase binding agent is selected from a group of materials consisting of: magnetic particulate, cellulose, glass, latexes, plastics, agaroses, sepharoses, and sephadexes.

9. The method of claim 5, wherein said solid phase is in the form of tubes.

10. The method of claim 5, wherein said solid phase is in the form of rods.

11. The method of claim 5, wherein said solid phase is in the form of spheres.

12. The method of claim 5, wherein said solid phase is in the form of particles.

13. The method of claim 5, wherein said fluorophores are selected from a group consisting of: fluorescein, dansyl, rhodamine, fluorescamine, pyrene, 2-methoxy-2,4-diphenyl-3(2H)-furanone, acradine and fluorescein mercuric acetate.

14. The method of claim 5, further comprising the step of:
    (f) comparing the measured fluorescent level with a standard fluorescent level.

* * * * *